US00PP27632P2

(12) United States Plant Patent
Hurd

(10) Patent No.: US PP27,632 P2
(45) Date of Patent: Jan. 31, 2017

(54) *VERONICA* PLANT NAMED 'WHITE WANDS'

(50) Latin Name: ***Veronica* hybrid**
Varietal Denomination: White Wands

(71) Applicant: Kevin A. Hurd, Austin, TX (US)

(72) Inventor: Kevin A. Hurd, Austin, TX (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 14/757,171

(22) Filed: Nov. 30, 2015

(51) Int. Cl.
*A01H 5/02* (2006.01)

(52) U.S. Cl.
USPC ..... Plt./251

(58) Field of Classification Search
None
See application file for complete search history.

*Primary Examiner* — Annette Para

(57) ABSTRACT

The new and distinct cultivar of hybrid ornamental spiked speedwell plant *Veronica* 'White Wands' with compact habit with upright habit and stiff, upright, heavily-branched spikes producing numerous, self-cleaning, white flowers over a long period without vernalization and suitable as a potted plant, for the garden, and for cut flower arrangements.

1 Drawing Sheet

Botanical classification: *Veronica* hybrid.
Variety denomination: 'White Wands'.

BACKGROUND OF THE INVENTION

The present invention relates to the new and distinct cultivar of spiked speedwell, botanically known as *Veronica* hybrid, and hereinafter also referred to by the cultivar name 'White Wands' or "the plant". The new plant selected as an individual seedling from a large population of seeds from a cross by Kevin A. Hurd between *Veronica alpina* 'Alba' (not patented) times *Veronica spicata* 'White' (a non-patented selection of white flowering *V. spicata*) on Aug. 4, 2009 at a wholesale perennial nursery in Zeeland, Mich., USA and originally referenced with the breeder code "K9-02-01." Seed was collected on Oct. 8, 2009, with the original plant evaluated over several years at the same nursery in Zeeland, Mich.

The plant has been asexually propagated by basal shoot tip cuttings in the greenhouses at the same nursery in Zeeland, Mich., with subsequent asexually propagated plants found to be identical to the original selection with all the same traits as the original seedling.

No plants have been sold, in this country or anywhere in the world, prior to the filing of this application, nor has any disclosure been made prior to the filing of this application with the exception of that which was disclosed within one year of the filing of this application and was either derived directly or indirectly from the inventor.

BRIEF SUMMARY OF THE PLANT

*Veronica* 'White Wands' is unique from all other spiked speedwell known to the inventor. Several other cultivars have white flowers, but this is the only variety known by the applicant to have the following trait combinations.

Compared to the female parent, *Veronica alpina* 'Alba', the new plant is more upright and taller, with more branched scapes.

Compared to the male parent, *Veronica spicata* 'White', the new plant is more compact and shorter and has an extended flowering season with better ability to repeat flower.

Other comparison varieties with white flowers known to the inventor are *Veronica* 'Whitewater' U.S. Plant Pat. No. 22,783, *Veronica* 'Icicle' (not patented), *Veronica* 'Alllady' U.S. Plant Pat. No. 23,271, *Veronica* 'Charlotte' U.S. Plant Pat. No. 23,803, *Veronica* 'Melanie White' (not patented), *Veronica* 'Atomic White' U.S. Plant Pat. No. 23,937, *Veronica* 'Agriverowhi' U.S. Plant Pat. No. 24,784 and *Veronica* 'Verswhite' U.S. Plant Pat. No. 24,177. Besides the differences in Table 1 below, 'Charlotte' also has variegated foliage, 'Atomic White' has light pink to white flowers and broader habit and both 'Agriverowhi' and 'Verswhite' have smaller leaves.

Table 1 below shows a more concise comparison of some of the other nearest spike speedwell cultivars:

TABLE 1

| Cultivar | plant height | raceme length | total flowers | 1° stem | 2° stem |
|---|---|---|---|---|---|
| *V. spicata* 'Icicle' | 66 cm | 15 cm | 125 | 125 | 0 |
| *V. spicata* 'White' | 60 cm | 15 cm | 120 | 120 | 0 |
| *V.* hybrid 'White Wands' | 56 cm | 27.5 cm | 1225 | 325 | 200 |
| *V. alpina* 'Alba' | 20 cm | 10 cm | 120 | 120 | 0 |
| *V.* hybrid 'Whitewater' U.S. Plant Pat. 22,783 | 15 cm | 6 cm | 12 | 12 | 0 |
| *V. longifolia* 'Alllady' U.S. Plant Pat. 23,271 | 59 cm | 9.5 cm | 1495 | 235 | 140 |
| *V. longifolia* 'Charlotte' U.S. Plant Pat. 23,803 | 42 cm | 10.6 cm | 210 | 210 | 0 |
| *V. longifolia* 'Melanie White' | 45 cm | 12 cm | 240 | 240 | 0 |
| *V. longifolia* 'Atomic White' U.S. Plant Pat. 23,937 | 50 cm | 17.4 cm | 1000 | 700 | 75 |
| *V. spicata* 'Agriverowhi' | 30 cm | 10 cm | 120 | 120 | 0 |
| *V. spicata* 'Verswhite' | 32 cm | 15 cm | 165 | 165 | 0 |

The following are traits of *Veronica* 'White Wands' that in combination distinguish it from all other spiked speedwell known to the inventor:

1. Upright habit, well-branched scapes producing continuous heavy flower show.
2. Numerous self-cleaning white flowers.
3. Freely flowering requiring no vernalization.
4. Lanceolate foliage of bright green remaining on plant without premature lower leaf drop.

BRIEF DESCRIPTION OF THE DRAWINGS

The photograph of the new plant demonstrates the overall appearance and unique traits of 'White Wands' as a two-year old plant grown in a full-sun trial garden in Zeeland, Mich. with supplemental water and fertilizer provided as needed.

The colors are as accurate as reasonably possible with color reproductions. Variation in ambient light spectrum, source and direction may cause the appearance of minor variation in color.

DETAILED BOTANICAL DESCRIPTION

Figure 1:
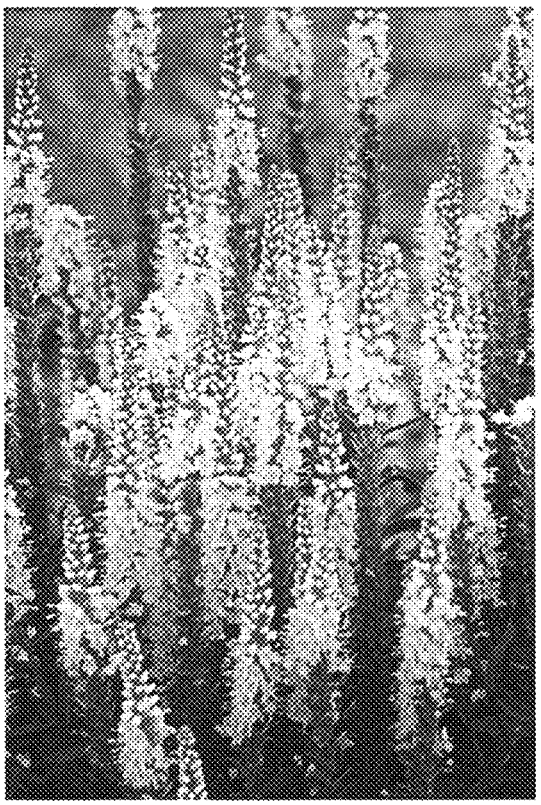
FIG. 1 shows a close-up of the scape and flowers.
Figure 2:
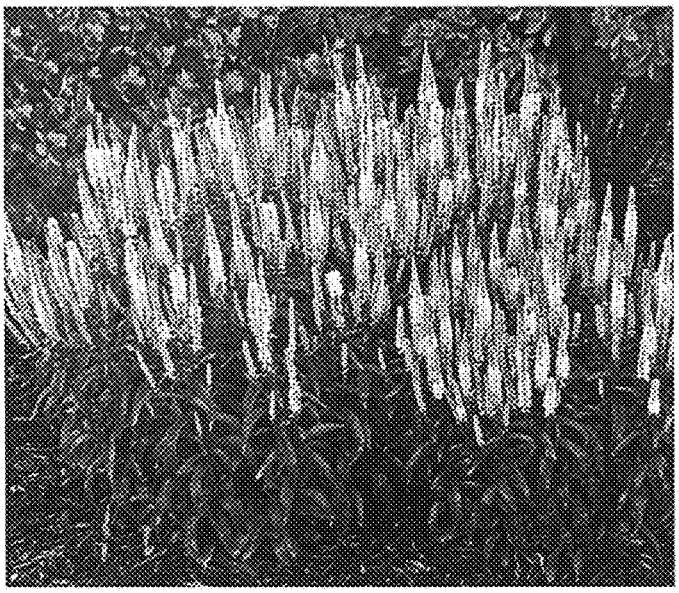
FIG. 2 shows three plants in the landscape in midsummer.

The following descriptions and color references of a greenhouse-grown one-year old plant of 'White Wands' are based on the 2001 edition of The Royal Horticultural Society Colour Chart except where common dictionary terms are used. *Veronica* 'White Wands' has not been observed under all possible environments. The phenotype may vary slightly with different growing environments such as temperature, light, fertility, soil pH, moisture and maturity levels, but without any change in the genotype. The following observations and size descriptions are based on two-year old plants in the full-sun trial garden of a nursery in Zeeland, Mich. with supplemental fertilizer and water as needed.

Botanical classification: *Veronica* hybrid.

Parentage: Female (seed parent) *Veronica alpina* 'Alba' (not patented); male (pollen parent) *Veronica spicata* 'White'.

Plant habit: Hardy herbaceous perennial, upright, freely branching, average about 28.0 cm tall at top of foliage and with flowers about 56.0 cm tall, about 30 cm wide; flowering beginning early July in Michigan and continuing for about 5 weeks with consistent repeat if deadheaded.

Stem: About six per plant; glabrous in lower portion, puberulent in distal portion; stiff, nearly vertical; to 56.0 cm tall, average about 42.7 cm tall; to about 4.0 mm diameter at base, average about 3.8 mm.

Stem color: Between RHS 144A and RHS 146 below flowers.

Nodes: About 8 before flowers; internode length about 3.0 cm, greater distally; color same as surrounding stem.

Leaves: Simple, flat, lanceolate, opposite, serrate, mature leaves glabrous adaxial and puberulent abaxial, young leaves puberulent abaxial and adaxial; acute apex, attenuate base; average about 6.5 cm long by about 2.5 cm wide decreasing in both length and width distally; surfaces dull, becoming vernicose adaxial with maturity.

Leaf size: To about 9.5 cm long and about 3.0 cm wide; average about 8.5 cm long and about 2.2 cm wide.

Leaf color: Young adaxial nearest RHS 143A, abaxial between RHS 143A and RHS 143B; mature adaxial nearest RHS 137A and abaxial between RHS 138A and RHS 138B.

Veins: Pinnate, glabrous, midrib adaxial slightly impressed, abaxial ridged.

Vein color: Adaxial midrib nearest RHS 145B, secondary veins nearest RHS 137A; abaxial midrib between RHS 145B and RHS 145C, secondary veins nearest RHS 137B.

Petiole: Simple, concavo-convex, glabrous both surfaces; to about 7.0 mm long and about 6.0 mm wide at base, distally shorter; average about 6.0 mm long and about 5.0 mm wide.

Petiole color: Adaxial side nearest RHS 137B toward distal margin, center and base nearest RHS 139C; abaxial nearest RHS 144D at margin and base, and between RHS 143A and RHS 143B on margins.

Buds two days prior to opening: Ovoid; acute apex and rounded base; about 5.0 mm long and 2.0 mm diameter.

Bud color: White, lighter than RHS 155C or RHS 155D.

Flowers: Zygomorphic, campanulate, complete; in many-flowered virgate raceme about 2.0 cm across; each flower subtended by bract; individual flowers effective for about one week; mainly outwardly facing; congested; numerous, approximately 325 per main peduncle and about 150 and 50 flowers per primary and secondary branch respectively with a total of about 1250 per raceme; self-cleaning; fragrance not detected.

Flower size: About 6.0 mm across and about 8.0 mm long.

Petals: Four; margin entire; oblanceolate; acute apex; glabrous and dull both surfaces; fused in basal 3.0 mm; largest petal above and smallest below; largest petal about 5.0 mm long by about 3.0 mm wide; smallest petal about 5.0 mm long and about 2.0 mm wide; side petals about 5.0 long and 2.5 mm wide.

Petal colors: White, lighter than RHS 155D; base nearest RHS 145D.

Androecium: Two, exserted.

*Filaments*.—Glabrous; adnate about 2.0 mm from base of corolla; about 4.0 mm long by 0.5 mm diameter; color white, lighter than RHS 155D.

*Anther*.—Elliptic; dorsifixed, longitudinal with acute apex and rounded base; about 2.0 mm long by about 1.0 mm diameter; color nearest RHS 10D.

*Pollen*.—Abundant, globose, less than 0.1 mm; color between RHS 158D and RHS 11D.

Gynoecium: Single; simple.

*Style*.—Single; curved downward in young flowers, straight and extending perpendicular to flower face in older flowers; about 5.5 mm long by about 0.25 mm diameter; color white, lighter than RHS 155D; persists after petals drop.

*Stigma*.—Semi-spherical; about 0.5 mm in diameter; color nearest RHS 155D.

*Ovary*.—Superior; puberulent; globose to elliptic; about 0.8 mm in diameter and 1.0 mm tall; color nearest RHS 144A.

Calyx: Campanulate to rotate; about 2.5 mm long and 3.0 mm across at apex; fused in basal 0.5 mm.

Sepals: Four; entire, surfaces dull, lanceolate, acute apex, base fused, puberulent abaxial, glabrous adaxial.

Sepal color: Nearest RHS 137A abaxial and adaxial.

Peduncle: Strong, stiff, erect, terete, puberulent; to about 35.0 cm long, average about 27.0 cm long and about 3.0 mm in diameter at the base; primary branches about 14 cm long and 2.0 mm diameter; secondary branches about 4.5 cm long and 1.5 mm diameter; primary and secondary branch angle about 65 to 75 degrees from horizontal; up to ten branches per main peduncle.

Peduncle color: Between RHS 144A and RHS 146C.

Pedicel: Upright to nearly 45 degree angle; rigid, terete; about 1.0 mm long and 0.5 mm diameter, puberulent.

Pedicel color: Nearest RHS 138A.

Bract: Single subtending each flower, lanceolate, acute apex, entire, sessile, based fused to peduncle, proximal bracts to about 2.4 cm long and about 4.0 mm wide and decreasing distally to about 3.0 mm long and less than about 0.5 mm wide.

Bract color: Adaxial nearest RHS 139A and abaxial between RHS 137A and RHS 137B.

Fruit: Emarginate, globose, puberulent, loculicidal capsule; about 3.0 mm diameter.

Seed: Elliptic, about 1.0 mm long; between RHS 166A and RHS 166B.

Propagation: Stem and tip cuttings root in about 2 weeks and finish to flowering in a 3.8 liter container in 8 to 10 weeks following a vernalization period of about 8 weeks.

Hardiness, pest and disease resistance: The plant grows best with adequate moisture and drainage, but is able to tolerate some drought when mature. Hardiness at least from USDA zone 4 through 8. Maintains lower leaves throughout season better than many other spiked speedwell. Other disease and pest resistance beyond what is typical of that common to other spiked speedwell has not been observed.

I claim:

1. A new and distinct cultivar of ornamental spiked speedwell plant, *Veronica* 'White Wands', as herein described and illustrated.

* * * * *